(12) United States Patent
Salahieh et al.

(10) Patent No.: US 9,393,094 B2
(45) Date of Patent: Jul. 19, 2016

(54) TWO-PART PACKAGE FOR MEDICAL IMPLANT

(75) Inventors: Amr Salahieh, Saratoga, CA (US); Tom Saul, El Granada, CA (US); Robert Geshlider, San Francisco, CA (US); Andrea Johnson, Saratoga, CA (US); Dwight Morejohn, Davis, CA (US); Daniel Hildebrand, Menlo Park, CA (US); Jean-Pierre Dueri, Los Gatos, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 873 days.

(21) Appl. No.: 13/367,733

(22) Filed: Feb. 7, 2012

(65) Prior Publication Data

US 2012/0132547 A1    May 31, 2012

Related U.S. Application Data

(60) Continuation of application No. 12/777,161, filed on May 10, 2010, now Pat. No. 8,136,659, which is a division of application No. 11/275,913, filed on Feb. 2, 2006, now Pat. No. 7,712,606.

(60) Provisional application No. 60/716,883, filed on Sep. 13, 2005.

(51) Int. Cl.
*B65D 73/00* (2006.01)
*A61F 2/00* (2006.01)
(Continued)

(52) U.S. Cl.
CPC ............. *A61F 2/0095* (2013.01); *A61F 2/2427* (2013.01); *A61F 2002/9517* (2013.01)

(58) Field of Classification Search
USPC ................. 206/438, 63.5, 363, 370
See application file for complete search history.

(56) References Cited

U.S. PATENT DOCUMENTS 3,334,629 A   8/1967   Cohn
3,409,013 A   11/1968  Berry
(Continued)

FOREIGN PATENT DOCUMENTS

CN   1338951 A   3/2002
EP   0409929 B1  4/1997
(Continued)

OTHER PUBLICATIONS

Andersen, H.R. et al. "Transluminal implantation of artificial heart valves. Description of a new expandable aortic valve and initial results with implantation by catheter technique in closed chest pigs." Quro. Heart J. 1992; 13:704-708.
(Continued)

*Primary Examiner* — Jacob K Ackun
(74) *Attorney, Agent, or Firm* — Seager, Tufte & Wickhem LLP

(57) ABSTRACT

The invention provides a two-part package and method of use for a pre-attached medical implant and delivery tool system. The package includes a wet compartment and a dry compartment and allows a pre-attached implant and delivery tool system to be at least partially stored immersed in a fluid in the wet compartment and at least partially stored in the dry compartment. In one embodiment the implant comprises a replacement heart valve, and the heart valve is stored inside the wet compartment while the heart valve delivery tool remains dry in the dry compartment.

5 Claims, 15 Drawing Sheets

(51) Int. Cl.
*A61F 2/24* (2006.01)
*A61F 2/95* (2013.01)

(56) References Cited

U.S. PATENT DOCUMENTS

| | | | |
|---|---|---|---|
| 3,540,431 A | 11/1970 | Mobin-Udin | |
| 3,628,535 A | 12/1971 | Ostrowsky et al. | |
| 3,642,004 A | 2/1972 | Osthagen et al. | |
| 3,657,744 A | 4/1972 | Ersek | |
| 3,671,979 A | 6/1972 | Moulopoulos | |
| 3,795,246 A | 3/1974 | Sturgeon | |
| 3,839,741 A | 10/1974 | Haller | |
| 3,868,956 A | 3/1975 | Alfidi et al. | |
| 3,874,388 A | 4/1975 | King et al. | |
| 4,056,854 A | 11/1977 | Boretos et al. | |
| 4,106,129 A | 8/1978 | Carpentier et al. | |
| 4,233,690 A | 11/1980 | Akins | |
| 4,291,420 A | 9/1981 | Reul | |
| 4,326,306 A | 4/1982 | Poler | |
| 4,423,809 A | 1/1984 | Mazzocco | |
| 4,425,908 A | 1/1984 | Simon | |
| 4,501,030 A | 2/1985 | Lane | |
| 4,542,825 A * | 9/1985 | Thomas et al. | 206/363 |
| 4,580,568 A | 4/1986 | Gianturco | |
| 4,585,453 A * | 4/1986 | Martin et al. | 623/2.11 |
| 4,602,911 A | 7/1986 | Ahmadi et al. | |
| 4,610,688 A | 9/1986 | Silvestrini et al. | |
| 4,617,932 A | 10/1986 | Kornberg | |
| 4,647,283 A | 3/1987 | Carpentier et al. | |
| 4,648,881 A | 3/1987 | Carpentier et al. | |
| 4,655,218 A * | 4/1987 | Kulik et al. | 606/207 |
| 4,655,771 A | 4/1987 | Wallsten | |
| 4,662,885 A | 5/1987 | DiPisa, Jr. | |
| 4,665,906 A | 5/1987 | Jervis | |
| 4,710,192 A | 12/1987 | Liotta et al. | |
| 4,733,665 A | 3/1988 | Palmaz | |
| 4,755,181 A | 7/1988 | Igoe | |
| 4,796,629 A | 1/1989 | Grayzel | |
| 4,819,751 A | 4/1989 | Shimada et al. | |
| 4,834,755 A | 5/1989 | Silvestrini et al. | |
| 4,856,516 A | 8/1989 | Hillstead | |
| 4,865,600 A | 9/1989 | Carpentier et al. | |
| 4,872,874 A | 10/1989 | Taheri | |
| 4,909,252 A | 3/1990 | Goldberger | |
| 4,917,102 A | 4/1990 | Miller et al. | |
| 4,954,126 A | 9/1990 | Wallsten | |
| 4,986,830 A | 1/1991 | Owens et al. | |
| 4,994,077 A | 2/1991 | Dobben | |
| 5,002,556 A | 3/1991 | Ishida et al. | |
| 5,002,559 A | 3/1991 | Tower | |
| 5,064,435 A | 11/1991 | Porter | |
| 5,161,547 A | 11/1992 | Tower | |
| 5,163,953 A | 11/1992 | Vince | |
| 5,209,741 A | 5/1993 | Spaeth | |
| 5,258,042 A | 11/1993 | Mehta | |
| 5,332,402 A | 7/1994 | Teitelbaum | |
| 5,336,258 A | 8/1994 | Quintero et al. | |
| 5,350,398 A | 9/1994 | Pavcnik et al. | |
| 5,370,685 A | 12/1994 | Stevens | |
| 5,389,106 A | 2/1995 | Tower | |
| 5,397,351 A | 3/1995 | Pavcnik et al. | |
| 5,403,305 A * | 4/1995 | Sauter et al. | 606/1 |
| 5,411,552 A | 5/1995 | Andersen et al. | |
| 5,425,762 A | 6/1995 | Muller | |
| 5,431,676 A | 7/1995 | Dubrul et al. | |
| 5,443,495 A | 8/1995 | Buscemi et al. | |
| 5,443,499 A | 8/1995 | Schmitt | |
| 5,443,502 A * | 8/1995 | Caudillo et al. | 623/2.11 |
| 5,476,506 A | 12/1995 | Lunn | |
| 5,476,510 A | 12/1995 | Eberhardt et al. | |
| 5,480,423 A | 1/1996 | Ravenscroft et al. | |
| 5,507,767 A | 4/1996 | Maeda et al. | |
| 5,534,007 A | 7/1996 | St. Germain et al. | |
| 5,545,133 A | 8/1996 | Burns et al. | |
| 5,545,211 A | 8/1996 | An et al. | |
| 5,549,665 A | 8/1996 | Vesely et al. | |
| 5,554,185 A | 9/1996 | Block et al. | |
| 5,560,487 A * | 10/1996 | Starr | 206/438 |
| 5,571,215 A | 11/1996 | Sterman et al. | |
| 5,575,818 A | 11/1996 | Pinchuk | |
| 5,645,559 A | 7/1997 | Hachtman et al. | |
| 5,662,671 A | 9/1997 | Barbut et al. | |
| 5,667,523 A | 9/1997 | Bynon et al. | |
| 5,674,277 A | 10/1997 | Freitag | |
| 5,693,083 A | 12/1997 | Baker et al. | |
| 5,695,498 A | 12/1997 | Tower | |
| 5,713,953 A | 2/1998 | Vallana et al. | |
| 5,716,370 A | 2/1998 | Williamson, IV et al. | |
| 5,720,391 A | 2/1998 | Dohm et al. | |
| 5,733,325 A | 3/1998 | Robinson et al. | |
| 5,735,842 A | 4/1998 | Krueger et al. | |
| 5,769,812 A | 6/1998 | Stevens et al. | |
| 5,800,456 A | 9/1998 | Maeda et al. | |
| 5,807,405 A | 9/1998 | Vanney et al. | |
| 5,817,126 A | 10/1998 | Imran | |
| 5,824,041 A | 10/1998 | Lenker et al. | |
| 5,824,043 A | 10/1998 | Cottone, Jr. | |
| 5,824,053 A | 10/1998 | Khosravi et al. | |
| 5,824,055 A | 10/1998 | Spiridigliozzi et al. | |
| 5,824,056 A | 10/1998 | Rosenberg | |
| 5,824,064 A | 10/1998 | Taheri | |
| 5,843,158 A | 12/1998 | Lenker et al. | |
| 5,855,597 A | 1/1999 | Jayaraman | |
| 5,855,601 A | 1/1999 | Bessler et al. | |
| 5,860,966 A | 1/1999 | Tower | |
| 5,861,024 A | 1/1999 | Rashidi | |
| 5,861,028 A | 1/1999 | Angell | |
| 5,868,783 A | 2/1999 | Tower | |
| 5,876,448 A | 3/1999 | Thompson et al. | |
| 5,885,228 A | 3/1999 | Rosenman et al. | |
| 5,888,201 A | 3/1999 | Stinson et al. | |
| 5,891,191 A | 4/1999 | Stinson | |
| 5,895,399 A | 4/1999 | Barbut et al. | |
| 5,907,893 A | 6/1999 | Zadno-Azizi et al. | |
| 5,910,154 A | 6/1999 | Tsugita et al. | |
| 5,911,734 A | 6/1999 | Tsugita et al. | |
| 5,925,063 A | 7/1999 | Khosravi | |
| 5,944,738 A | 8/1999 | Amplatz et al. | |
| 5,954,766 A | 9/1999 | Zadno-Azizi et al. | |
| 5,957,949 A | 9/1999 | Leonhardt et al. | |
| 5,968,070 A | 10/1999 | Bley et al. | |
| 5,984,957 A | 11/1999 | Laptewicz, Jr. et al. | |
| 5,984,959 A | 11/1999 | Robertson et al. | |
| 5,993,469 A | 11/1999 | McKenzie et al. | |
| 5,997,557 A | 12/1999 | Barbut et al. | |
| 6,010,522 A | 1/2000 | Barbut et al. | |
| 6,022,370 A | 2/2000 | Tower | |
| 6,027,520 A | 2/2000 | Tsugita et al. | |
| 6,027,525 A | 2/2000 | Suh et al. | |
| 6,042,598 A | 3/2000 | Tsugita et al. | |
| 6,042,607 A | 3/2000 | Williamson, IV et al. | |
| 6,093,203 A | 7/2000 | Uflacker | |
| 6,123,723 A | 9/2000 | Konya et al. | |
| 6,142,987 A | 11/2000 | Tsugita | |
| 6,162,245 A | 12/2000 | Jayaraman | |
| 6,165,200 A | 12/2000 | Tsugita et al. | |
| 6,165,209 A | 12/2000 | Patterson et al. | |
| 6,168,579 B1 | 1/2001 | Tsugita | |
| 6,171,327 B1 | 1/2001 | Daniel et al. | |
| 6,179,859 B1 | 1/2001 | Bates | |
| 6,187,016 B1 | 2/2001 | Hedges et al. | |
| 6,197,053 B1 | 3/2001 | Cosgrove et al. | |
| 6,200,336 B1 | 3/2001 | Pavcnik et al. | |
| 6,214,036 B1 | 4/2001 | Letendre et al. | |
| 6,221,006 B1 | 4/2001 | Dubrul et al. | |
| 6,221,091 B1 | 4/2001 | Khosravi | |
| 6,221,096 B1 | 4/2001 | Aiba et al. | |
| 6,231,544 B1 | 5/2001 | Tsugita et al. | |
| 6,231,551 B1 | 5/2001 | Barbut | |
| 6,241,757 B1 | 6/2001 | An et al. | |
| 6,245,102 B1 | 6/2001 | Jayaraman | |
| 6,251,135 B1 | 6/2001 | Stinson et al. | |
| 6,258,114 B1 | 7/2001 | Konya et al. | |
| 6,258,115 B1 | 7/2001 | Dubrul | |

(56) References Cited

U.S. PATENT DOCUMENTS

| | | |
|---|---|---|
| 6,258,120 B1 | 7/2001 | McKenzie et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,348,063 B1 | 2/2002 | Yassour et al. |
| 6,352,708 B1 | 3/2002 | Duran et al. |
| 6,361,545 B1 | 3/2002 | Macoviak et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,303 B1 | 10/2002 | Amplatz et al. |
| 6,475,239 B1 | 11/2002 | Campbell et al. |
| 6,482,228 B1 | 11/2002 | Norred |
| 6,485,502 B2 | 11/2002 | Don Michael et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,537,297 B2 | 3/2003 | Tsugita et al. |
| 6,540,768 B1 | 4/2003 | Diaz et al. |
| 6,562,058 B2 | 5/2003 | Seguin et al. |
| 6,592,546 B1 | 7/2003 | Barbut et al. |
| 6,592,614 B2 | 7/2003 | Lenker et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford et al. |
| 6,712,843 B2 | 3/2004 | Elliott |
| 6,714,842 B1 | 3/2004 | Ito |
| 6,719,789 B2 | 4/2004 | Cox |
| 6,723,122 B2 | 4/2004 | Yang et al. |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,773,454 B2 | 8/2004 | Wholey et al. |
| 6,776,791 B1 | 8/2004 | Stallings et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,814,746 B2 | 11/2004 | Thompson et al. |
| 6,821,297 B2 | 11/2004 | Snyders |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,953,332 B1 | 10/2005 | Kurk et al. |
| 6,964,673 B2 | 11/2005 | Tsugita et al. |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,122,020 B2 | 10/2006 | Mogul |
| 7,166,097 B2 | 1/2007 | Barbut |
| 7,175,653 B2 | 2/2007 | Gaber |
| 7,175,654 B2 | 2/2007 | Bonsignore et al. |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,258,696 B2 | 8/2007 | Rabkin et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,445,631 B2 | 11/2008 | Haug et al. |
| 7,632,298 B2 | 12/2009 | Hijkema et al. |
| 7,699,168 B2 | 4/2010 | Ryan et al. |
| 7,712,606 B2 | 5/2010 | Salahieh et al. |
| 7,722,666 B2 | 5/2010 | Lafontaine |
| 7,748,389 B2 | 7/2010 | Salahieh |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson, IV et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029981 A1 | 3/2002 | Nigam |
| 2002/0032481 A1 | 3/2002 | Gabbay |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0151970 A1 | 10/2002 | Garrison et al. |
| 2002/0161392 A1 | 10/2002 | Dubrul |

(56) References Cited

U.S. PATENT DOCUMENTS

| | | |
|---|---|---|
| 2002/0161394 A1 | 10/2002 | Macoviak et al. |
| 2002/0177766 A1 | 11/2002 | Mogul |
| 2002/0188341 A1 | 12/2002 | Elliott |
| 2002/0188344 A1 | 12/2002 | Bolea et al. |
| 2003/0023303 A1 | 1/2003 | Palmaz et al. |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0045928 A1 | 3/2003 | Yang et al. |
| 2003/0050694 A1 | 3/2003 | Yang et al. |
| 2003/0055495 A1 | 3/2003 | Pease et al. |
| 2003/0060844 A1 | 3/2003 | Borillo et al. |
| 2003/0070944 A1 * | 4/2003 | Nigam .................. 206/210 |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149476 A1 | 8/2003 | Damm et al. |
| 2003/0149478 A1 | 8/2003 | Figulla et al. |
| 2003/0168370 A1 | 9/2003 | Merboth et al. |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri et al. |
| 2004/0088045 A1 | 5/2004 | Cox |
| 2004/0093016 A1 | 5/2004 | Root et al. |
| 2004/0098022 A1 | 5/2004 | Barone |
| 2004/0098099 A1 | 5/2004 | McCullagh et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0181140 A1 | 9/2004 | Falwell et al. |
| 2004/0186563 A1 | 9/2004 | Lobbi |
| 2004/0204755 A1 | 10/2004 | Robin |
| 2004/0215331 A1 | 10/2004 | Chew et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0254636 A1 | 12/2004 | Flagle et al. |
| 2005/0033402 A1 | 2/2005 | Cully et al. |
| 2005/0043711 A1 | 2/2005 | Corcoran et al. |
| 2005/0075662 A1 | 4/2005 | Pedersen et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0096692 A1 | 5/2005 | Linder et al. |
| 2005/0096734 A1 | 5/2005 | Majercak et al. |
| 2005/0096735 A1 | 5/2005 | Hojelbane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Panlagua et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137696 A1 | 6/2005 | Salahieh et al. |
| 2005/0137697 A1 | 6/2005 | Salahieh et al. |
| 2005/0137699 A1 | 6/2005 | Salahieh et al. |
| 2005/0137701 A1 | 6/2005 | Salahieh et al. |
| 2005/0143809 A1 | 6/2005 | Salahieh et al. |
| 2005/0165352 A1 | 7/2005 | Henry et al. |
| 2005/0165477 A1 | 7/2005 | Anduiza et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203614 A1 | 9/2005 | Forster |
| 2005/0203615 A1 | 9/2005 | Forster |
| 2005/0203616 A1 | 9/2005 | Cribier |
| 2005/0203617 A1 | 9/2005 | Forster et al. |
| 2005/0209580 A1 | 9/2005 | Freyman |
| 2005/0228472 A1 | 10/2005 | Case et al. |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0015177 A1 | 1/2006 | Quest et al. |
| 2006/0058872 A1 | 3/2006 | Salahieh et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0260967 A1 | 11/2006 | Clarke et al. |
| 2006/0271166 A1 | 11/2006 | Thill et al. |
| 2006/0287668 A1 | 12/2006 | Fawzi et al. |
| 2007/0010876 A1 | 1/2007 | Salahieh et al. |
| 2007/0010877 A1 | 1/2007 | Salahieh et al. |
| 2007/0016286 A1 | 1/2007 | Hermann et al. |
| 2007/0055340 A1 | 3/2007 | Pryor |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0203503 A1 | 8/2007 | Salahieh et al. |
| 2007/0244552 A1 | 10/2007 | Salahieh et al. |
| 2008/0125859 A1 | 5/2008 | Salahieh et al. |
| 2008/0188928 A1 | 8/2008 | Salahieh et al. |
| 2008/0234814 A1 | 9/2008 | Salahieh et al. |
| 2008/0288054 A1 | 11/2008 | Pulnev et al. |
| 2009/0054969 A1 | 2/2009 | Salahieh et al. |
| 2009/0076598 A1 | 3/2009 | Salahieh et al. |
| 2009/0222076 A1 | 9/2009 | Figulla et al. |
| 2009/0264997 A1 | 10/2009 | Haug et al. |
| 2010/0280495 A1 | 11/2010 | Paul et al. |

FOREIGN PATENT DOCUMENTS

| | | | |
|---|---|---|---|
| EP | | 1000590 A1 | 5/2000 |
| EP | | 1057459 A1 | 12/2000 |
| EP | | 1057460 A1 | 12/2000 |

(56) References Cited

FOREIGN PATENT DOCUMENTS

| | | |
|---|---|---|
| EP | 0937439 A2 | 9/2003 |
| EP | 1340473 A2 | 9/2003 |
| EP | 1356793 A2 | 10/2003 |
| EP | 1042045 A1 | 5/2004 |
| EP | 0819013 A1 | 6/2004 |
| EP | 1229864 B1 | 4/2005 |
| EP | 1430853 A2 | 6/2005 |
| EP | 1059894 A2 | 7/2005 |
| EP | 1078610 A2 | 8/2005 |
| EP | 1576937 A2 | 9/2005 |
| EP | 1582178 A2 | 10/2005 |
| EP | 1582179 A2 | 10/2005 |
| EP | 1469797 A1 | 11/2005 |
| EP | 1600121 A1 | 11/2005 |
| EP | 1156757 A2 | 12/2005 |
| EP | 1616531 A2 | 1/2006 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9836790 A1 | 8/1998 |
| WO | 9850103 A1 | 11/1998 |
| WO | 9857599 A2 | 12/1998 |
| WO | 9944542 A2 | 9/1999 |
| WO | 0009059 A2 | 2/2000 |
| WO | 0044308 A2 | 8/2000 |
| WO | 0044313 A1 | 8/2000 |
| WO | 0049970 A1 | 8/2000 |
| WO | 0067661 A2 | 11/2000 |
| WO | 0105331 A1 | 1/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0164137 A1 | 9/2001 |
| WO | 0236048 A1 | 5/2002 |
| WO | 0241789 A2 | 5/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03030776 A2 | 4/2003 |
| WO | 03015851 A1 | 11/2003 |
| WO | 03094797 A1 | 11/2003 |
| WO | 2004014256 A1 | 2/2004 |
| WO | 2004019811 A2 | 3/2004 |
| WO | 2004023980 A2 | 3/2004 |
| WO | 2004026117 A2 | 4/2004 |
| WO | 2004041126 A1 | 5/2004 |
| WO | 2004047681 A1 | 6/2004 |
| WO | 2004066876 A1 | 8/2004 |
| WO | 2004082536 A1 | 9/2004 |
| WO | 2005084595 A1 | 9/2005 |
| WO | 2005087140 A1 | 9/2005 |

OTHER PUBLICATIONS

Atwood, A. et al. "Insertion of Heart Valves by Catheterization." Project Supervised by Prof. S. Muftu of Northeastern University 2001-2002: 36-40.
Bodnar, E. et al. Replacement Cardiac Valves R Chapter 13: Extinct cardiac valve prostheses. Pergamon Publishing Corporation. New York, 1991: 307-322.
Boudjemline, Y. et al. Percutaneous implantation of a biological valve in the aorta to treat aortic valve insufficiency—a sheep study.f Med Sci. Monit. 2002; vol. 8, No. 4: BR113-116.
Boudjemline, Y. et al. "Percutaneous implantation of a valve in the descending aorta in lambs." Euro. Heart J. 2002; 23: 1045-1049.
Boudjemline, Y. et al. "Percutaneous pulmonary valve replacement in a large right ventricular outflow tract: an experimental study." Journal of the American College of Cardiology. 2004; vol. 43(6): 1082-1087.
Boudjemline, Y. et al. "Percutaneous valve insertion: A new approach?" J. of Thoracic and Cardo. Sugr. 2003; 125 (3): 741-743.
Boudjemline, Y. et al. "Steps Toward Percutaneous Aortic Valve Replacement." Circulation. 2002; 105: 775-778.
Cribier, A. et al. "Early Experience with Percutaneous Transcatheter Implantation of Heart Valve Prosthesis for the Treatment of End-Stage Inoperable Patents with Calcific Aortic Stenosis." J. of Am. Coll. of Cardio. 2004; 43(4): 698-703.
Cribier, A. et al. "Percutaneous Transcatheter Implantation of an Aortic Valve Prosthesis for Calcific Aortic Stenosis: First Human Case Description." Circulation. 2002; 106: 3006-3008.
Cribier, A. et al. "Percutaneous Transcatheter Implantation of an Aortic Valve Prosthesis for Calcific Aortic Stenosis: First Human Case." Percutaneous Valve Technologies, Inc. 2002: 16 pages.
Ferrari, M. et al. "Percutaneous transvascular aortic valve replacement with self expanding stent-valve device." Poster from the presentation given at SMIT 2000, 12th International Conference. Sep. 5, 2000.
Hijazi, Z.M. "Transcatheter Valve Replacement: A New Era of Percutaneous Cardiac Intervention Begins." J. of Am. College of Cardio. 2-4; 43(6): 1088-1089.
Huber, C.H. et al. "Do valved stents compromise coronary flow?" European Journal of Cardio-thoracic Surgery. 2-4; vol. 25: 754-759.
Knudsen, L. L. et al. "Catheter-implanted prosthetic heart valves." Int'l J. of Art. Organs. 1993; 16(5): 253-262.
Kort, S. et al. "Minimally invasive aortic valve replacement: Echocardiographic and clinical results." Am Heart J. 2001; 142(3): 476-481.
Love, C. et al. The Autogenous Tissue Heart Valve: Current Stat.f Journal of Cardiac Surgery. 1991; 6(4): 499-507.
Lutter, G. et al. "Percutaneous aortic valve replacement: An experimental study. I. Studies on implantation." J. of Thoracic and Cardio. Surg. 2002; 123(4): 768-776.
Moulopoulos, S. D. et al. "Catheter-Mounted Aortic Valves." Annals of Thoracic Surg. 1971; 11(5): 423-430.
Paniagua, D. et al. "Percutaneous heart valve in the chronic in vitro testing model." Circulation. 2002; 106: e51-e52.
Paniagua, D. et al. Heart Watch (2004). Texas Heart Institute. Spring, 2004 Edition: 8 pages.
Pavcnik, D. et al. "Percutaneous bioprosthetic veno valve: A long-term study in sheep." J. of Vascular Surg. 2002; 35 (3): 598-603.
Phillips, S. J. et al. "A Temporary Catheter-Tip Aortic Valve: Hemodynamic Effects on Experimental Acute Aortic Insufficiency." Annals of Thoracic Surg. 1976; 21(2): 134-136.
Sochman, J. et al. "Percutaneous Transcatheter Aortic Disc Valve Prosthesis Implantation: A Feasibility Study." Cardiovasc. Intervent. Radiol. 2000; 23:384-388.
Stuart, M. "In Heart Valves, A Brave, New Non-Surgical World." Start-Up. 2004: 9-17.
Vahanian, A. et al. "Percutaneous Approaches to Valvular Disease." Circulation. 2004; 109: 1572-1579.
Van Herwerden, L. A. et al. "Percutaneous valve implantation: back to the future?" Euro. Heart J. 2002; 23(18): 1415-1416.
Zhou, J.Q. et al. "Self-expandable valved stent of large size: off-bypass implantation in pulmonary position." Eur. J. Cardiothorac. 2003; 24: 212-126.

* cited by examiner

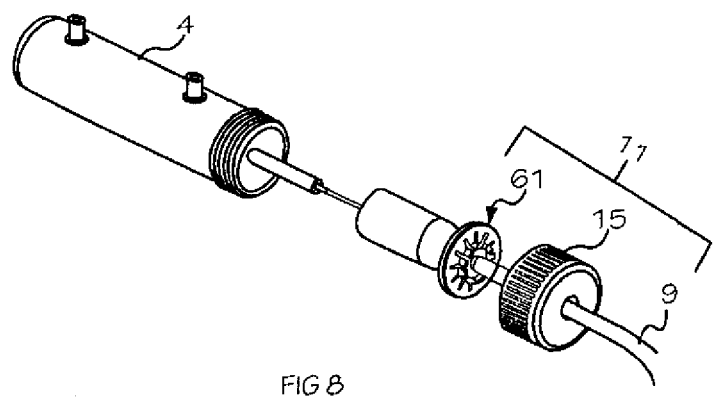
FIG 8
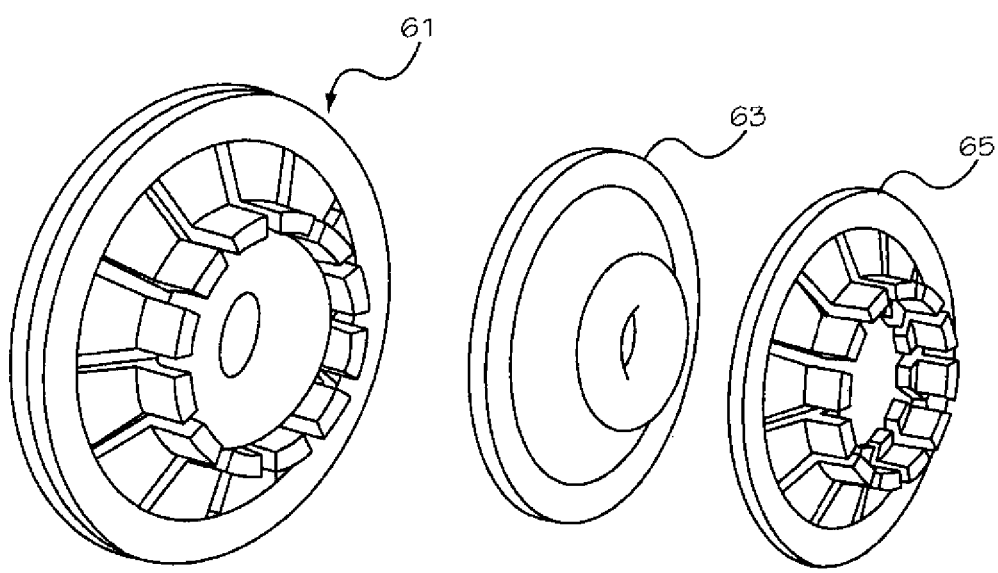
FIG 9
FIG 10

TWO-PART PACKAGE FOR MEDICAL IMPLANT

CROSS-REFERENCE

This application is a continuation of U.S. application Ser. No. 12/777,161, filed May 10, 2010, which is a divisional of U.S. application Ser. No. 11/275,913, filed Feb. 2, 2006, now U.S. Pat. No. 7,712,606; which application claims the benefit of U.S. Provisional Application No. 60/716,883, filed Sep. 13, 2005. These applications are incorporated herein by reference in their entirety.

BACKGROUND OF THE INVENTION

The present invention relates to packaging for medical implant and delivery tools, and specifically to packaging for pre-attached heart valve and delivery tool systems where the heart valve is stored in a fluid and at least part of the delivery tool is stored dry.

Percutaneously delivered tissue based replacement heart valves are typically packaged in a container filled with a storage solution. The storage solution is designed to maintain the biological integrity of the implant (e.g., implant functionality, sterility, and functional integrity) while stored and awaiting use. When needed for implanting in a patient, the container is opened and the valve is removed using a variety of techniques aimed at preventing damage to the valve. The storage solution in which the valve was stored is then rinsed from the valve to prepare it for use. Next, the valve is attached to a device that will facilitate delivery of the valve to the appropriate location in the patient's body. Additional implants may also benefit from being stored in a solution where a coating or treatment on the implant requires wet storage to maintain functionality.

SUMMARY OF THE INVENTION

It may be desirable to attach a medical implant to a delivery tool, thus forming a medical implant delivery system, at manufacture, prior to its storage and final use. Benefits provided by such pre-attached implant and delivery systems are in part described as follows. The risk of damage to the implant and delivery system resulting from the attachment procedure will be minimized since the procedure will be performed by experienced manufacturing technicians specifically trained for the task. The tools and environment will be set up specifically for the task. It will be possible to validate the performance of the implant system prior to final packaging. The preparation time required by the physician will be minimized thereby reducing the cost of the procedure. Thus, a pre-attached delivery system would make a medical implant surgery more cost effective, safer, and simpler.

As stated above, many heart valves are currently stored in a storage solution prior to use. Since a pre-attached implant and delivery tool provide benefits that an unattached implant and delivery tool do not, it becomes desirable to be able to store a pre-attached heart valve and delivery tool system for an extended period of time prior to the implant procedure. But while it is beneficial to store the implant in a storage solution, it is not always desirable to store the delivery tool in such a solution. To do so would require the wet storage container and volume of storage solution to be larger than required if only the implant is stored in solution. Furthermore, the delivery tool would have to tolerate exposure to the solution during storage, which places additional design constraints on materials for fabrication of the delivery tool. In addition, the added step of removing and rinsing the solution from the delivery tool prior to use would require additional time and complicates the use of the device. Thus, it becomes necessary to be able to store part of the pre-attached delivery system in a liquid medium, while keeping another part dry. Specifically, it is desirable to keep the implant stored in fluid while the delivery tool remains dry.

When the valve is ready for implanting in a patient, it will often be inserted into the body in a collapsed configuration thereby minimizing the delivery cross section and accommodating anatomical limitations imposed by the particular paths followed within the body to the implant's intended location. This is specifically the case when an implant is meant to at least partially expand once inside the body to produce its intended effect. When an implant's configuration is capable of being altered between such expanded and collapsed states, it is often desirable to store the implant in a relaxed and expanded condition. Thus, when an implant delivery system as described above is stored for an extended period of time prior to use, it is desirable to maintain the implant in a relaxed and at least a partially expanded configuration during storage. Maintaining an expanded configuration will preserve the biological functionality of the implant, thus making an implant surgery more effective.

The present invention provides packages and methods of packaging for a pre-attached medical implant and delivery tool systems. The package allows the implant and delivery tool to be stored pre-attached to one another, such that the implant can be stored in a storage solution and the delivery tool can remain at least partially dry.

The package of one aspect of the present invention provides for wet and dry compartments such that a pre-attached implant delivery system can partially be stored in a fluid and partially stored dry. Specifically, the implant portion of the delivery system can be stored at least partially in a fluid while the delivery tool can be at least partially stored in the dry compartment. In some instances of the present invention, the implant comprises a heart valve which can be stored completely immersed in fluid contained in the wet compartment.

In some instances of the present invention the package comprises an interface between the wet and dry compartments. The interface may have a sealing mechanism to prevent fluid inside the wet compartment from leaking into the dry compartment. The seal between the wet compartment and dry compartment may comprise a seal ring compressed against the delivery tool. A seal may also be formed by a device inside the delivery tool which creates the seal. An exemplary device may be an inflatable member. Another device may be a compression driven device. In other instances of the present invention multiple seals may be used to form a system of seals which create an interface between the wet and a dry compartment. In one such instance one seal may be formed around an outside surface of the delivery system and another seal formed within some portion of the delivery tool. It is another feature of some embodiments of the invention that an interface between the dry and wet compartments comprises a strain relief mechanism that reduces the risk of breakage of the delivery tool resulting from its bending during storage and use.

Also a feature of some embodiments of the invention is the incorporation within the wet compartment of a mechanism to flush fluid from the wet compartment and or facilitate rinsing the implant with a rinsing solution within the wet compartment prior to the implant's use.

In another embodiment the implant is substantially centered within the wet compartment by features in the wet compartment.

In yet another embodiment the wet compartment incorporates features which minimize the amount of storage solution required to keep the implant submerged irrespective of the orientation of the package.

In another embodiment the wet compartment has an upper and a lower housing, and may have at least two gaskets between the housings. In some instances there may be only one gasket.

Another aspect of the invention provides a method of packaging a pre-attached medical implant and delivery tool by providing an implant pre-attached to a delivery tool, wet and dry package compartments, and loading the implant at least partially into the wet compartment such that the delivery tool is at least partially stored in the dry compartment. In one embodiment the implant is loaded into the wet compartment in a first configuration and reconfigured to a second configuration. The implant may be covered by a sheath in the first configuration and not covered by a sheath in the second configuration.

Yet another aspect of the invention provides a method of unpacking a pre-attached medical implant and delivery tool system from a package. In one embodiment the method includes providing an implant pre-attached to a delivery tool such that at least part of the implant is stored immersed in fluid, and the delivery tool is at least partially stored in a dry compartment. Fluid in the wet compartment is then flushed from the wet compartment, possibly with a rinsing solution and or with air. The configuration of the implant is altered from one configuration to a second configuration, and the implant is removed from the wet compartment.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

FIG. 8 shows an embodiment of the wet compartment and seal mechanism.

FIGS. 9 and 10 provide a seal assembly used in the present invention.

Figure 1:
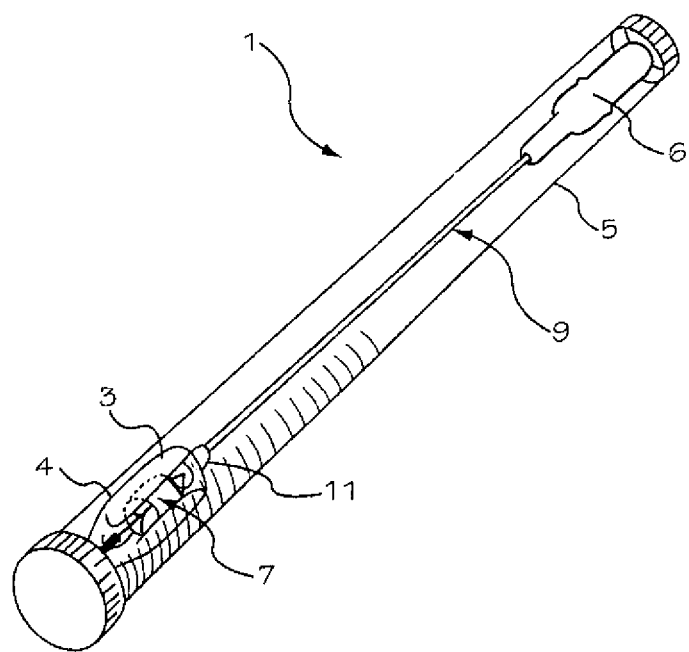
FIGS. 1 and 2 show alternative embodiments of a two-part package of the present invention.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

DETAILED DESCRIPTION OF THE INVENTION

The invention is drawn to a two-part packaging system for a medical implant delivery system. In some embodiments, the invention allows an implant to be pre-attached to a delivery tool and stored in an expanded and relaxed state in a storage solution while at least a portion of the delivery tool remains dry. The packaging system includes a wet compartment that is suitable for holding fluid and a dry compartment that remains dry, with a pass through between the two compartments to allow an implant delivery system to be stored partially in the wet compartment and partially in the dry compartment. This arrangement allows for the implant to be attached to the delivery tool prior to placement into the packaging system, creating a pre-attached implant delivery system. In one embodiment the implant portion of the delivery system is stored in the wet compartment and the delivery system is stored in the dry compartment. This arrangement allows the implant portion of the implant delivery system to be stored in fluid while preventing a portion of the delivery portion of the implant delivery system from being exposed to the fluid. In one embodiment of the invention the delivery system is comprised of a replacement heart valve connected to a delivery tool for delivering the heart valve to a desired located within a patient. The heart valve connected to the delivery tool may be stored inside the wet compartment while the delivery tool is stored inside the dry compartment. When the implant is ready for use the wet compartment may be drained of the fluid and or rinsed with a rinsing fluid, the implant can be removed from the packaging system and further prepared for use. This system thus simplifies, reduces risks of, and speeds the implant surgery because the delivery system is pre-attached prior to use and thus the user does not have to attach the implant to the delivery tool during the surgery. In still other embodiments the implant is stored partially in the wet compartment and partially in the dry compartment, and the delivery system is stored entirely in the dry compartment.

Possible implants envisioned for storage in the packaging system of the invention include those described in applications: Ser. No. 10/746,280 entitled "REPOSITIONABLE HEART VALVE AND METHOD," filed on Dec. 23, 2003; Ser. No. 10/893,131 entitled "METHODS AND APPARATUS FOR ENDOVASCULARLY REPLACING A PATIENT'S HEART VALVE" filed on Jul. 15, 2004; Ser. No. 10/893,151 entitled "METHODS AND APPARATUS FOR ENDOVASCULARLY REPLACING A PATIENT'S HEART VALVE" filed on Jul. 15, 2004; Ser. No. 10/746,120 entitled "EXTERNALLY EXPANDABLE HEART VALVE ANCHOR AND METHOD" filed on Dec. 23, 2003; Ser. No. 10/746,285 entitled "RETRIEVABLE HEART VALVE ANCHOR AND METHOD" filed Dec. 23, 2003; Ser. No. 10/982,692 entitled "METHODS AND APPARATUS FOR ENDOVASCULARLY REPLACING A HEART VALVE" filed on Nov. 5, 2004; Ser. No. 10/746,872 entitled "LOCKING HEART VALVE ANCHOR" filed on Dec. 23, 2003; and Ser. No. 10/870,340 entitled "EVERTING HEART VALVE" filed on Jun. 16, 2004.

Figure 2:
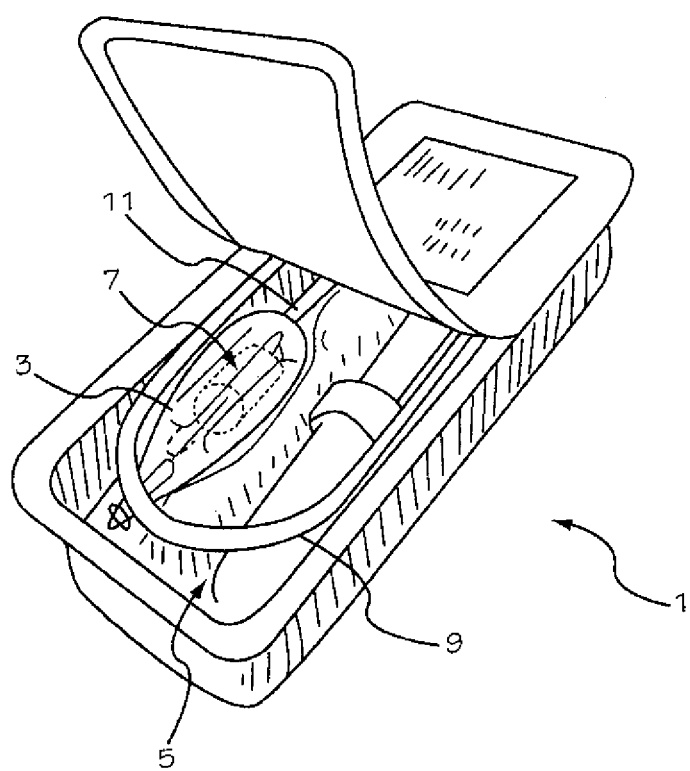

One embodiment of package 1 is shown in FIG. 1. Exemplary package 1 comprises a wet compartment 3, at least partially contained within container 4 and a dry compartment 5. The parts of an implant and its delivery system stored in wet and dry compartments may differ according to the materials, design, etc. of the implant and delivery system. In the embodiment shown in FIG. 1, an implant 7 is connected to a delivery tool 9 such that implant 7 is stored inside wet compartment 3, while delivery tool 9 and wet compartment 3 are stored inside the dry compartment 5. An interface 11 between the wet compartment 3 and the dry compartment 5 allows implant 7 to be connected to delivery tool 9 while storing implant 7 in a wet compartment 3 and keeping at least a portion of delivery tool 9 dry. Alternatively, a portion of the wet compartment may extend into the delivery tool and be additionally sealed within handle 6. In some embodiments the implant 7 may be partially stored inside the wet compartment 3. In other embodiments the delivery tool 9 may be partially stored in the dry compartment 5. In further embodiments implant 7 may be partially stored in the wet compartment and delivery tool 9 may be partially stored in the dry compartment. Package 1 may be cylindrical in shape, or may have a rectangular cross-section. The package may also be any other size, shape, or configuration that is suitable to store a pre-attached implant and delivery tool under the conditions of this invention. FIG. 2 shows another embodiment of package 1 where implant 7 is stored inside wet compartment 3 while delivery tool 9, which is connected to implant 7, and wet compartment 3 are stored inside dry compartment 5. The configurations of the delivery system shown in FIGS. 1 and 2 illustrate how at least key portions of the implant are maintained during storage in solution while at least part of the delivery tool remains dry and unexposed to the storage solution.

Figure 3:
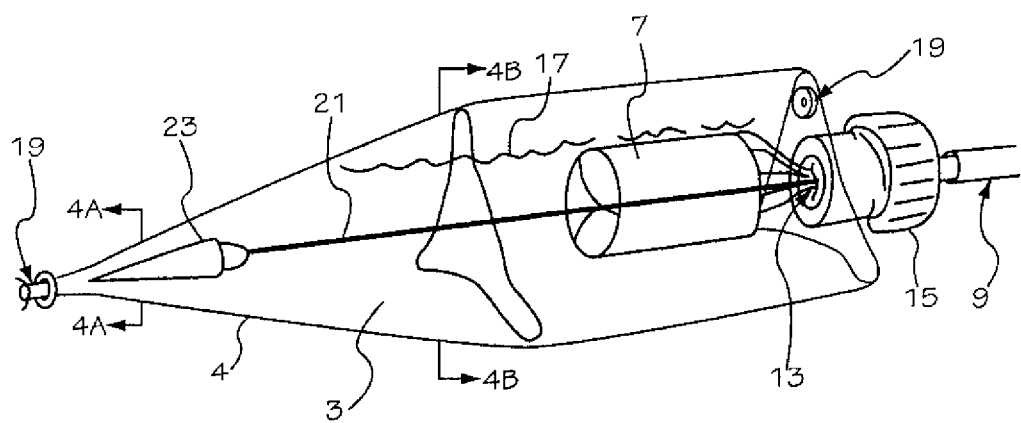
FIG. 3 illustrates an implant stored in a wet compartment immersed in fluid.

FIG. 3 shows one embodiment of wet container 4 comprising at least a portion of wet compartment 3. Delivery tool 9 comprising guide wire tube 21, which is connected to nose cone 23 is connected to implant 7. Implant 7 is stored inside wet compartment 3 which is filled with fluid 17 to keep the implant 7 wet during storage. Seal 13 prevents fluid 17 from escaping wet compartment 3. Exemplary wet container 4 has a part 19 with a luer connector used to flush and remove fluid 17 from wet compartment 3 prior to use of the implant. In some embodiments the wet compartment may comprise only one flushing part. In other embodiments the wet compartment may contain at least two or more flushing parts. FIG. 3 illustrates implant 7 in its expanded and relaxed configuration. This configuration is desirable during storage to maintain the biological functionality of the implant.

In some embodiments fluid 17 comprises a storage solution to preserve the functionality of implant 7 during storage in the package system. Fluid 17 may comprise a saline solution or any other storage solution. In some embodiments fluid 17 may comprise a sterilant and or fixative solution such as gluteraldehyde or formalin. In still other embodiments the fluid 17 may comprise a bacteria static solution to prevent bacteria from growing in the fluid. The fluid may also be a buffered solution. In some embodiments the solution may be comprised of a physiological salt or an alcohol. In further embodiments the fluid 17 may be any combination or mixture of the solutions described above, or any other solutions to achieve the intent of this invention.

In one embodiment the implant 7 comprises a replacement heart valve. In some embodiments the replacement heart valve may be comprised of tissue from a human, porcine, or other suitable animal. In some embodiments the heart valve may comprise a mechanical heart valve, bioprosthetic heart valve, polymer heart valve, or any other type of artificial heart valve treated in such a fashion as to require storage in a storage solution. In some embodiments the implant may comprise any combination of the above heart valves suitable for the present invention. In some embodiments implant 7 may also comprise implantable devices other than heart valves, for example, but not limited to, vascular grafts, angioplasty rings, and stents, musculoskeletal grafts, grafts specific to other body ducts including the digestive system or lymphatic system.

Figure 4A:
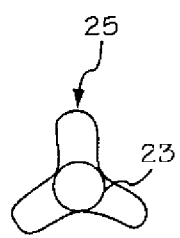
FIGS. 4A-B provide exemplary cross-sectional views of a wet compartment.
Figure 4B:
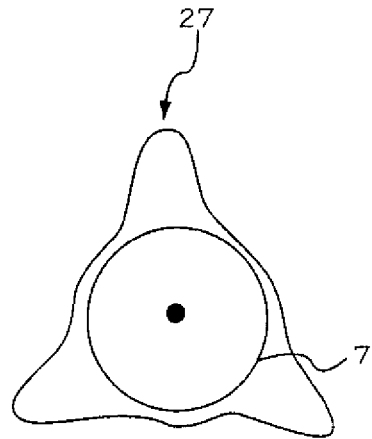
Figure 5A:
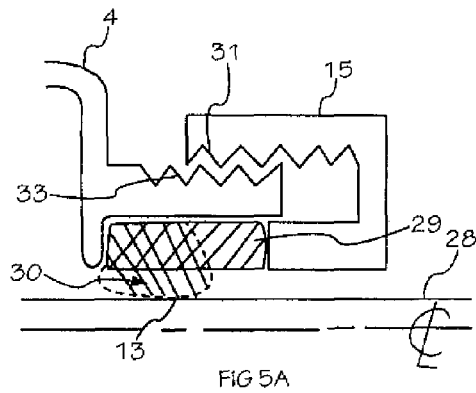
FIGS. 5A-G show seal systems that prevent fluid from escaping the wet compartment into the dry compartment.
Figure 5B:
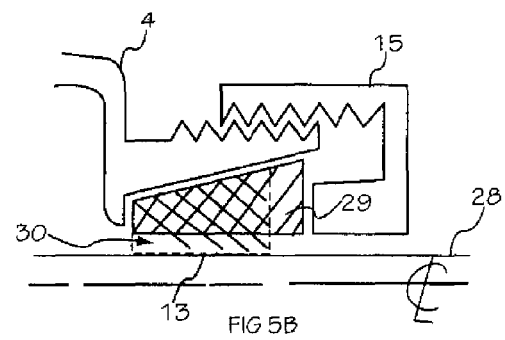
Figure 5C:
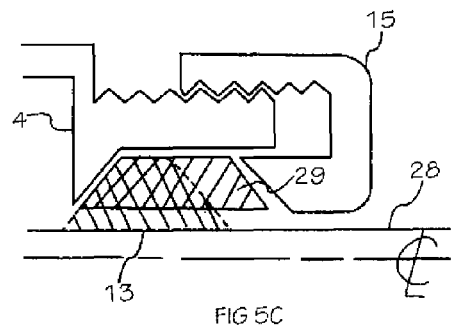
Figure 5D:
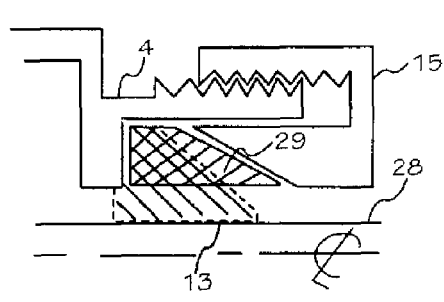
Figure 5E:
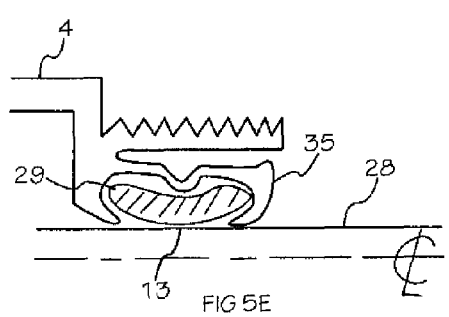
Figure 5F:
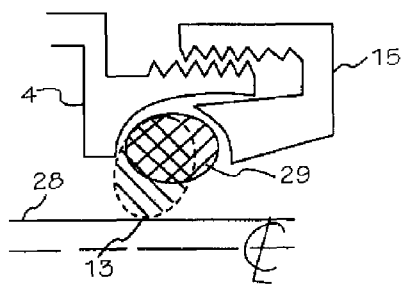
Figure 5G:
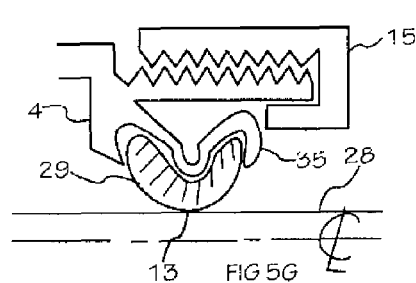

FIG. 4A shows an exemplary cross-section of the distal end of wet container 4 from FIG. 3, while FIG. 4B show a more proximally located cross-section of wet container 4 from FIG. 3. In some embodiments the cross-section of the wet compartment is triangular in shape. Such a shape minimizes the amount of fluid required to assure the implant is immersed in fluid over the range of possible orientations the container may be subjected to while in storage. A further benefit of the triangular shape or other non cylindrical shapes of the cross-section is to present a variable cross section of the fluid which acts as a mask for radiation. The wet container can then be designed to minimize the exposure to sterilizing radiation of portions of its contents. In other embodiments of the invention the cross section of the wet container may have a circular shape, a rectangular shape, or any other shape suitable for this invention. In further embodiments of the invention the wet container may have a combination of any of the above cross sectional shapes distributed across the wet container. The desired shape of the cross section of the wet compartment may depend on the type and size of the delivery system being stored in the package, the type and size of the implant stored in the wet compartment, both the type and size of the delivery system and the implant, the type of sterilization procedure, or any other factor. It is desirable that the size and shape of wet container 4 allows the implant 7 to be stored in an expanded and relaxed state during storage, allowing for greater biological functionality when the implant is inside a patient.

In some embodiments of the present invention a seal is formed between the dry compartment and wet compartment to prevent fluid inside the wet compartment from escaping into the dry compartment. A seal allows the implant to be stored in fluid to maintain its biological integrity, while keeping the delivery tool dry. An exemplary seal may be formed when a seal cap is screwed or attached onto a receiving member of the delivery system, forcing a compressing member against the delivery tool, creating the seal. FIGS. 5A-G illustrate similar embodiments of an exemplary seal that prevents fluid from entering the dry compartment of the packaging system. Exemplary seal 13 is created when seal ring 29 is compressed against the outer periphery of multi-lumen catheter 28 by compression fitting to fill space 30. Seal ring 29 is compressed when seal cap 15 is screwed onto wet container 4 such that male threads 31 of seal cap 15 engage female threads 33 of wet container 4. FIGS. 5A-E show exemplary configurations of seal ring 29 that may be used in the current invention to create a seal between the wet compartment and dry compartment. Any other suitable shape of seal ring may be used in accordance with this invention. In another embodiment shown in FIGS. 5F and 5G, seal ring 29 is compressed against the multi-lumen catheter 28 by folder member 35.

Figure 6:
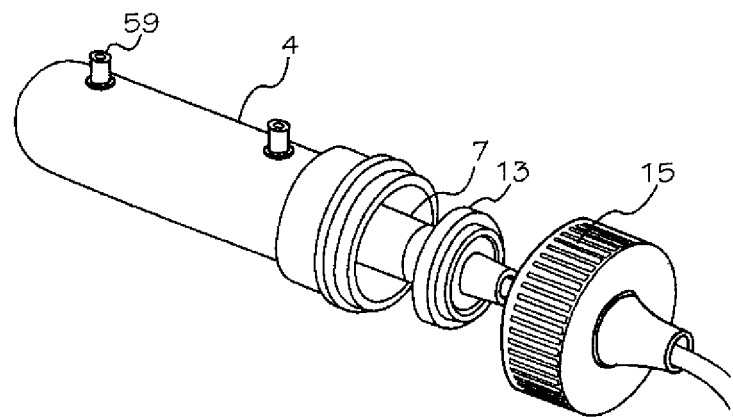
FIG. 6 shows a bottle and cap embodiment of the wet compartment and seal mechanism.
Figure 7:
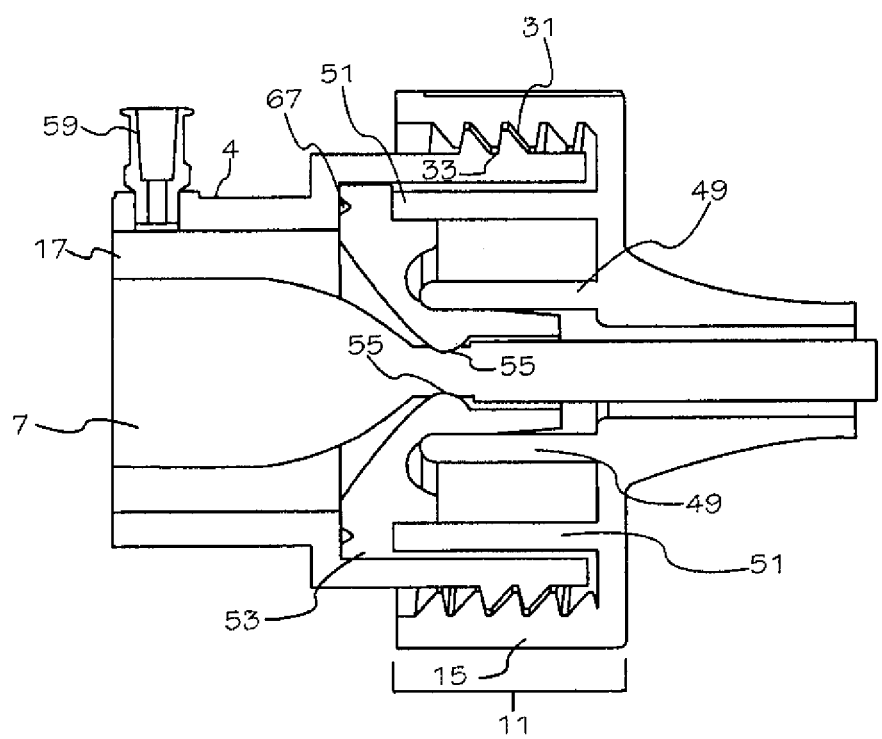
FIG. 7 illustrates an embodiment of the seal in which the seal is formed by compression fitting.
Figure 11:
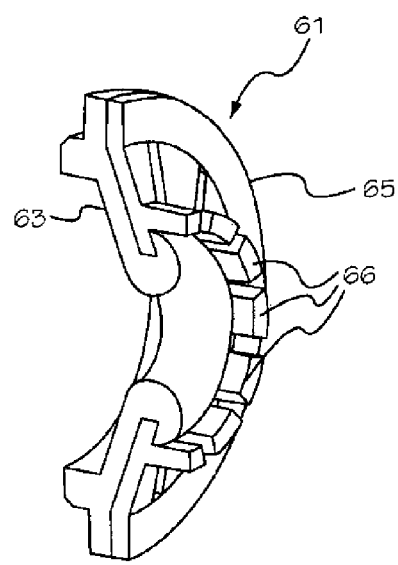
FIG. 11 shows a cross-sectional view of a seal assembly used in the invention.

FIG. 6 illustrates one embodiment of the invention using a bottle and cap assembly. Seal cap 15 is screwed onto bottle-shaped wet container 4 as described above to create the seal. The shape of wet container 4 allows the implant 7 to be stored in an expanded and relaxed state, but any other size, shape, or configuration of wet container 4 may be used to carry out the intent of the invention. FIG. 7 is a detailed sectional view of the seal mechanism depicted in FIG. 6. Exemplary seal cap 15 comprises seal cap arm 49, which causes elastomer compression fitting area 55 to compress against delivery tool 9 when seal cap 15 is screwed onto wet container 4, such that male threads 31 of seal cap 15 engage female threads 33 of wet container 4. When seal cap 15 is screwed onto wet container 4, seal cap arm 51 pushes elastomer compression fitting 53 against V-rib 67 of wet container 4, sealing the wet container 4 to elastomer compression fitting 53.

Figure 12:
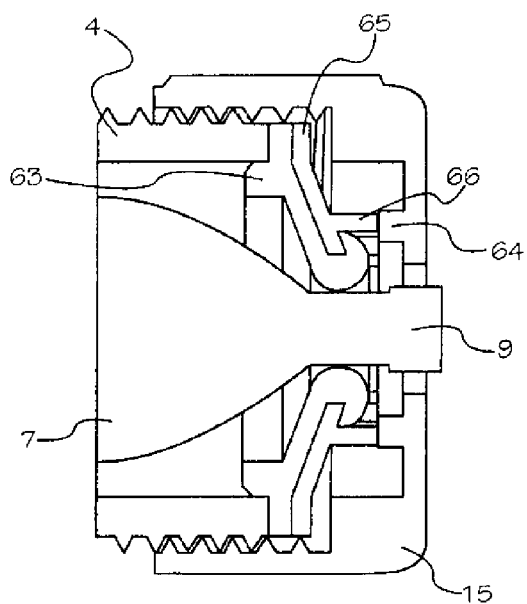
FIG. 12 shows an unloaded state of a seal.
Figure 13:
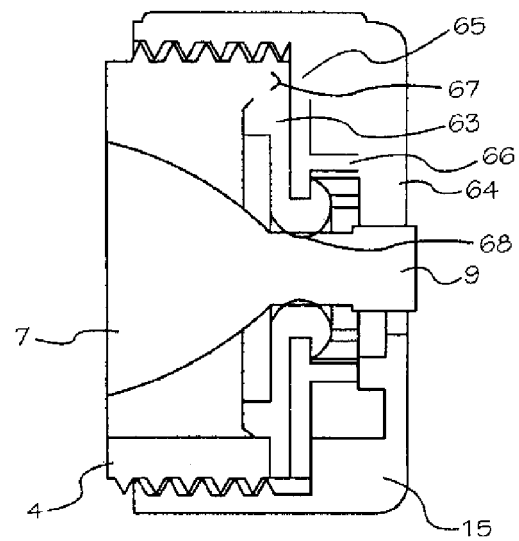
FIG. 13 illustrates a loaded state of a seal which prevents fluid from escaping the wet compartment.
Figure 14:
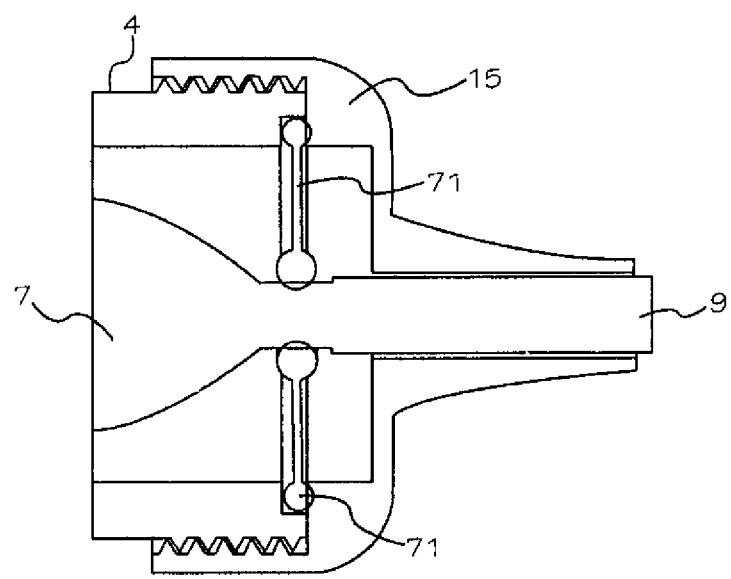
FIG. 14 shows an embodiment of the seal mechanism.

FIGS. 8-13 illustrate another embodiment of the interface 11 where seal assembly 61 is comprised of elastomer diaphragm 63 and plastic support spring 65. In FIG. 12, the seal assembly is shown in an unloaded state. In FIG. 13 seal cap 15 is screwed onto wet container 4, causing the inner rim 64 of seal cap 15 to push and straighten spring ridges 66 and elastomer diaphragm 63, compressing elastomer diaphragm area 68 against delivery tool 9, creating a seal. V-rib 67 of wet container 4 creates a seal between the wet container 4 and elastomer diaphragm 63 when seal cap 15 is completely screwed onto wet container 4. In another embodiment of the seal shown in FIG. 14, an exemplary seal against the delivery tool is maintained by the elasticity of the elastomer diaphragm seal 71. The seal cap 15 is screwed onto wet container 4 as described above, causing elastomer diaphragm seal 71 to be compressed against container 4. The examples of the seals above allow the implant to be at least partially stored in solution in the wet compartment of the delivery system while preventing fluid from escaping, thus keeping the delivery tool dry. The use of a seal further allows the implant to be pre-attached to the delivery tool such that the delivery tool can be kept at least partially dry during storage.

Figure 15A:
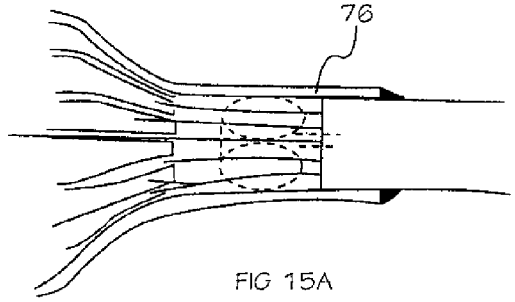
FIG. 15 illustrates a delivery tool seal.
Figure 15B:
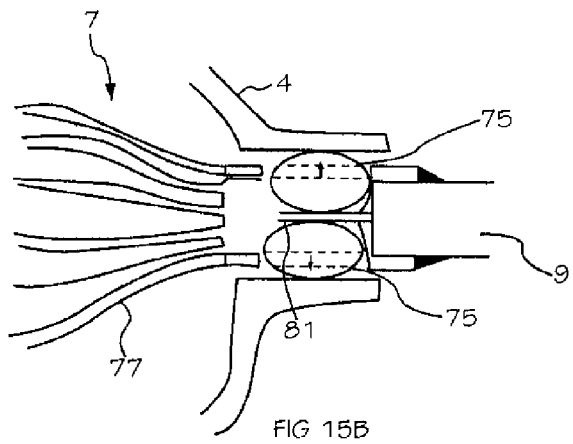
Figure 16A:
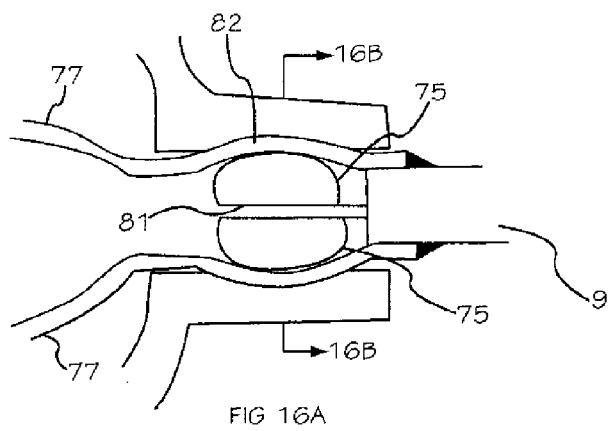
FIGS. 16A-B illustrates a delivery tool seal.
Figure 16B:
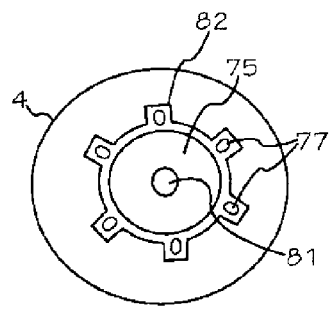

In other embodiments of the invention an additional seal between the wet compartment and the dry compartment may be required and is created by a device or mechanism inside the delivery tool. Referring to FIG. 15A, an exemplary seal is created by inflatably expanding member 75, collapsing multi lumens 77 of implant 7 against ring 76 the outer periphery of the distal end of the delivery tool. Alternatively as depicted in FIG. 15B, the exemplary seal created by inflatably expanding member 75, collapsing multi lumens 77 of implant 7, may seal against wet container 4. The inflatably expanding member 75 is inflated by central lumen 81 which is located within delivery tool 9. In some embodiments, the central lumen 81 inflates the inflatably expanding member 75 with air, liquid, or any other substance or gas that is suitable for the present invention. In another embodiment of the seal, FIGS. 16A and 16B show inflatably expanding member 75 pushing multi-lumens 77 of implant 7 into slots 82 within wet container 4 to create a smooth sealing surface. These exemplary seals prevent fluid inside the wet compartment from escaping into the dry part of the delivery system, allowing the implant to be stored in a storage solution while keeping at least a portion of the delivery tool dry.

Figure 17:
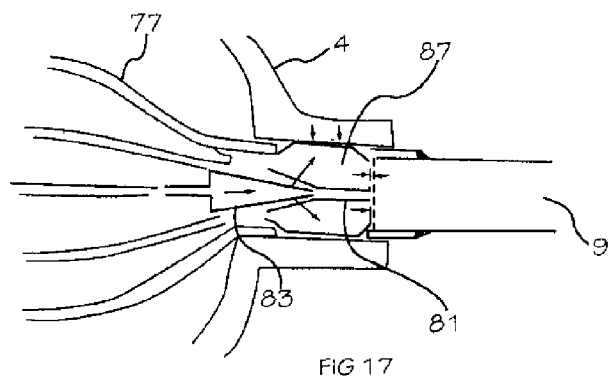
FIG. 17 show a delivery tool wedge compression seal.

In another embodiment shown in FIG. 17, the delivery tool 9 comprises a driven compression component 83 and elastomer compressible component 87, wherein, by forcing the compression component into the compressible component, the compression caused be component 83 against the compressed component 87 collapses multi-lumens 77 against the wet container 4, creating a seal between the wet compartment 3 and the dry compartment of the implant delivery system. In some embodiments of the invention, compression component 83 comprises a conical shape such that expanding member 83 wedges between elastomer 87, collapsing multi-lumens 77 against the wet container 4 to create the seal.

Figure 18A:
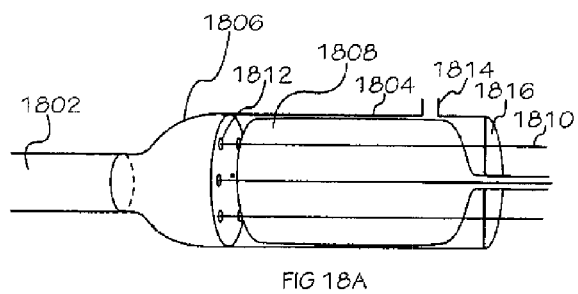
FIGS. 18A-G show an alternative seal located within the handle of the delivery tool.

In yet another embodiment the additional seal may be incorporated in the handle as depicted in FIGS. 18A-G. Such a seal may in addition incorporate an homeostatic seal which provides additional functionality to the implant deployment system. FIG. 18A shows an embodiment in which actuation elements 1810 extend from a chamber within the deployment tool handle 1804 into lumens 1812 extending through a tapered adapter portion 1806 into a catheter 1802 of the deployment tool. A balloon 1808 or other inflatable device may be inflated during storage to maintain any storage solution within catheter 1802 and lumens 1806 (and possibly surrounding any implant connected to the deployment tool). Balloon 1804 may be deflated prior to use to permit the storage fluid to be drained and or rinsed from the device through port 1814. During use, handle end cap 1816 provides a homeostatic seal permitting actuation elements 1810 but substantially preventing blood to escape from handle 1804. Such a homeostatic seal may be configured from a thin sheet of silicone through which the actuation elements pass. Wherein the interface between the silicone sheet and actuation elements comprises an interference fit.

Figure 18E:
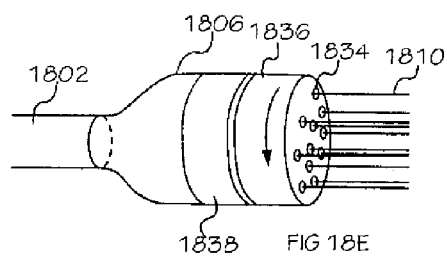
Figure 18B:
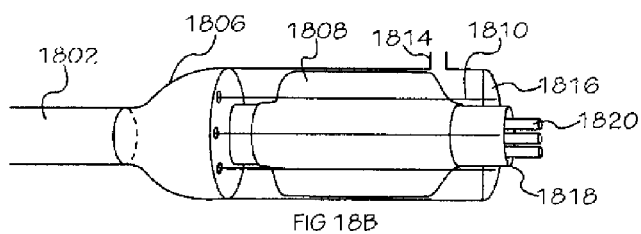

FIG. 18B shows an embodiment similar to that of FIG. 18A in which balloon 1808 has a central lumen 1818 permitting other devices (such as actuation elements 1820) to pass through toward the distal end of the deployment tool.

Figure 18F:
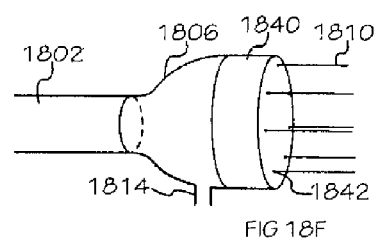
Figure 18C:
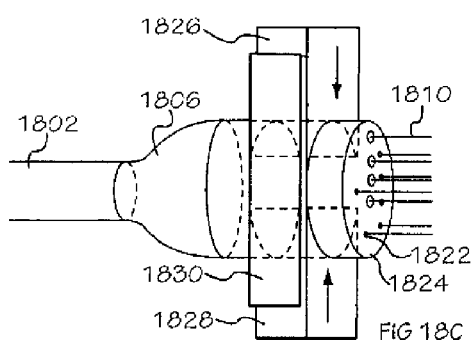

FIG. 18C shows an embodiment in which the actuation elements 1810 pass through holes 1822 formed in an elastomeric plug 1824. To seal the deployment tool system during storage, slidable bars 1826 and 1828 of a seal actuator are moved toward each other along a guide 1830 to compress plug 1824 and seal holes 1822 around actuation elements 1810. This action maintains storage fluid within catheter 1802 and around any implant connected to the deployment tool.

Figure 18G:
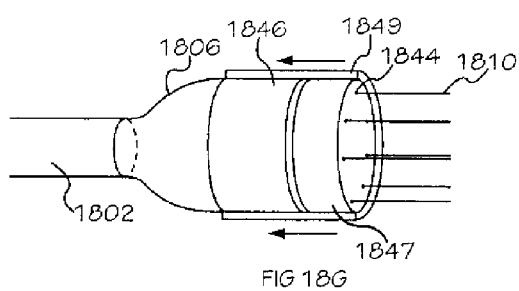
Figure 18D:
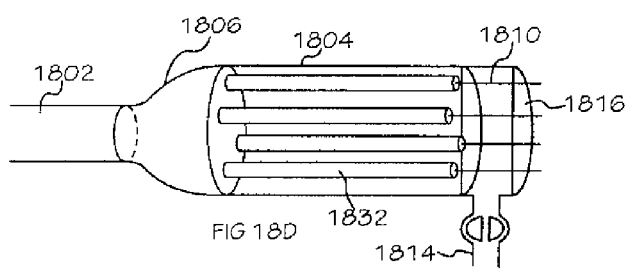

FIG. 18D shows an embodiment in which the actuation elements 1810 pass through flexible tubes 1832 within handle 1804. Pressurized fluid may be provided to the interior of handle 1804 through a valved port 1814 to collapse tubes 1832 around actuation elements 1810, thereby retaining any storage fluid within catheter 1802 (and around any attached implant) during storage. Storage fluid may be drained and or rinsed from the system by port 1814 before use of the deployment tool.

FIG. 18E shows an embodiment in which the actuation elements pass through holes (not shown) formed in handle portion 1838 and through holes 1834 formed in a rotating handle endpiece 1836. Rotation of endpiece 1836 in the direction shown takes holes 1834 out of alignment with their corresponding holes in handle portion 1838, thereby sealing in any storage fluid in the interior of tapered handle portion

1806 and catheter 1802 (and any attached implant). Endpiece 1836 may be rotated the other direction to line up the holes to permit actuation elements 1810 to be moved during use of the deployment tool.

FIG. 18F shows an embodiment in which the actuation elements 1810 pass through holes 1842 in an endpiece 1840 made at least in part of wax or low durometer elastomer or some frangible material. While in storage, holes 1842 seal around actuation elements 1810 to retain storage fluid within the deployment tool and any attached implant. Prior to use, storage fluid may be drained and or rinsed from the system through port 1814. Movement of actuation elements 1810 through holes 1842 breaks the seal formed by the frangible material, thereby permitting deployment tool to be used to deploy the implant.

FIG. 18G shows an embodiment in which the actuation elements 1810 pass through holes 1844 formed in an elastomeric plug 1846 extending from the proximal end of the deployment tool handle. Distal movement of plug 1847 (in the direction of the arrows) compresses plug 1846 against the surface of tapered handle portion 1806 and outer cylinder 1849. This action compresses holes 1844 against actuation elements 1810, thereby sealing the deployment tool and retaining any storage fluid within it.

Figure 19:
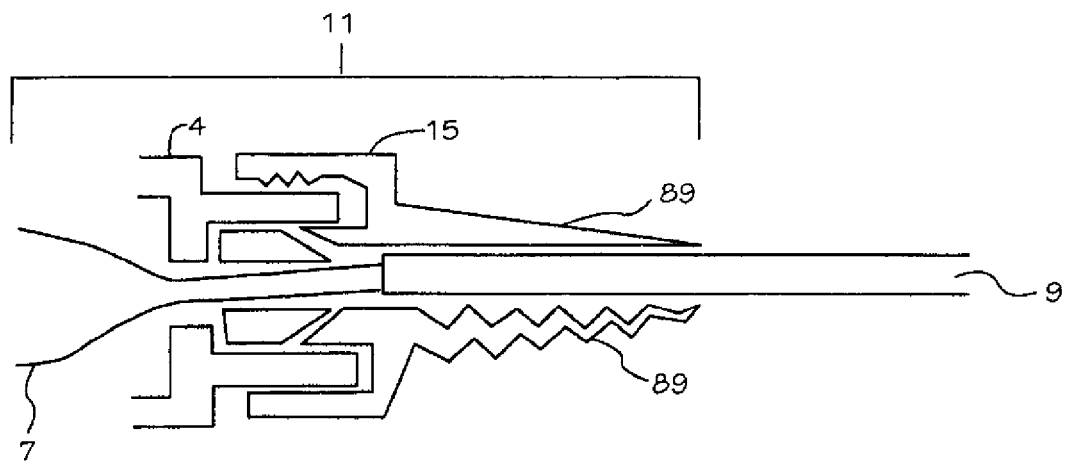
FIG. 19 shows a strain relief mechanism of the seal cap to protect the delivery tool during bending.

It is desirable that the delivery system can be stored, transported, and used without undergoing damage to the system due to bending from movement or manipulations from any number of sources. In a further embodiment of interface 11 as shown in FIG. 19, exemplary seal cap 15 comprises a strain relief feature embodied in component 89 to protect delivery tool 9 from damage due to small radius bends in the delivery tool 9 during storage and use. In some embodiments the strain relief component may be smooth, and in some embodiments the strain relief mechanism may have internal and external ribs. In some embodiments the strain relief component may be removably attached to the seal cap.

Figure 20:
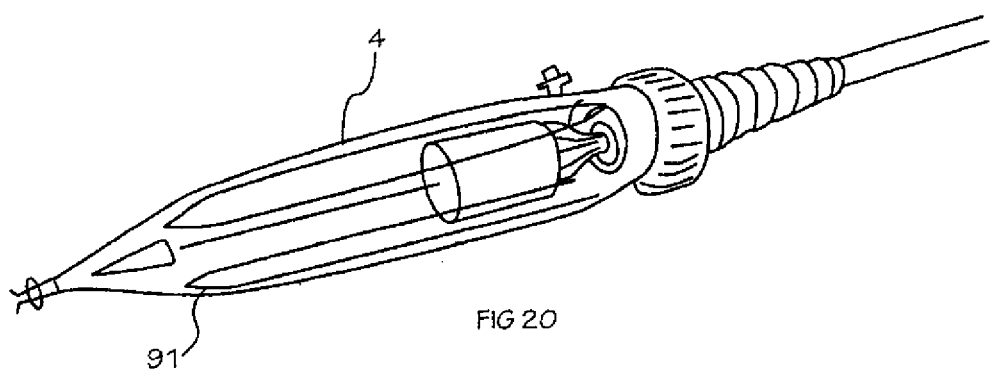
FIG. 20 shows an embodiment of a bottle style wet container for the package and a portion of the delivery system.
Figure 21:
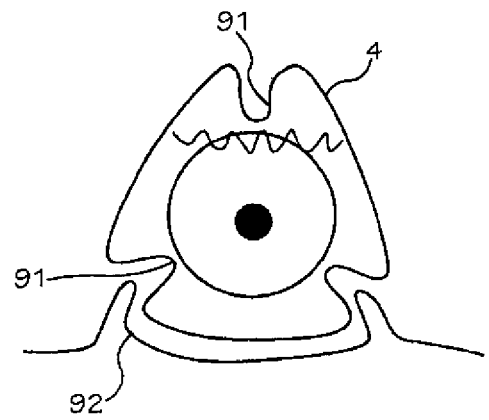
FIG. 21 shows an alternate cross section of a wet container for the package.

An alternate embodiment of wet container 4 as shown in FIGS. 20 and 21 incorporates infolded wings 91 within wet container 4 to provide the same functionality as that described for FIGS. 4A and 4B. Additional support of the infolded wings 91 may be provided by a backboard 92 on the device packaging, as shown in FIG. 21.

Figure 22:
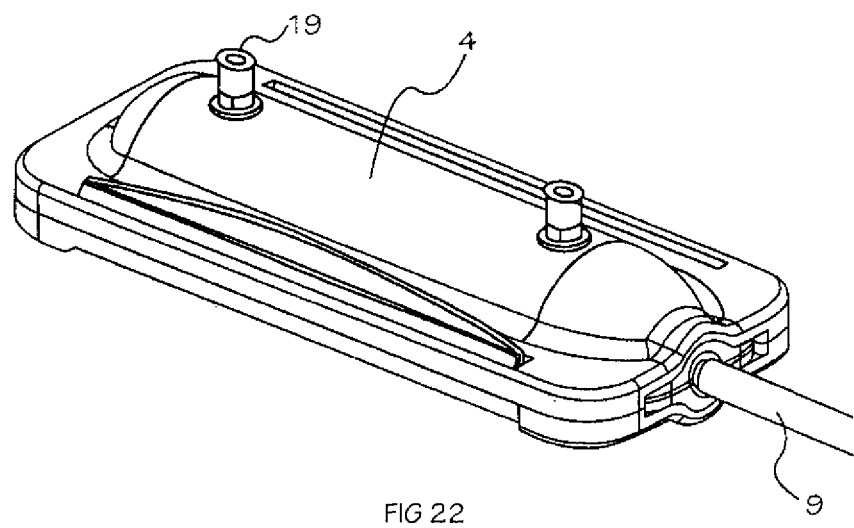
FIG. 22 illustrates a clam shell embodiment of a wet container for the package assembled.
Figure 23:
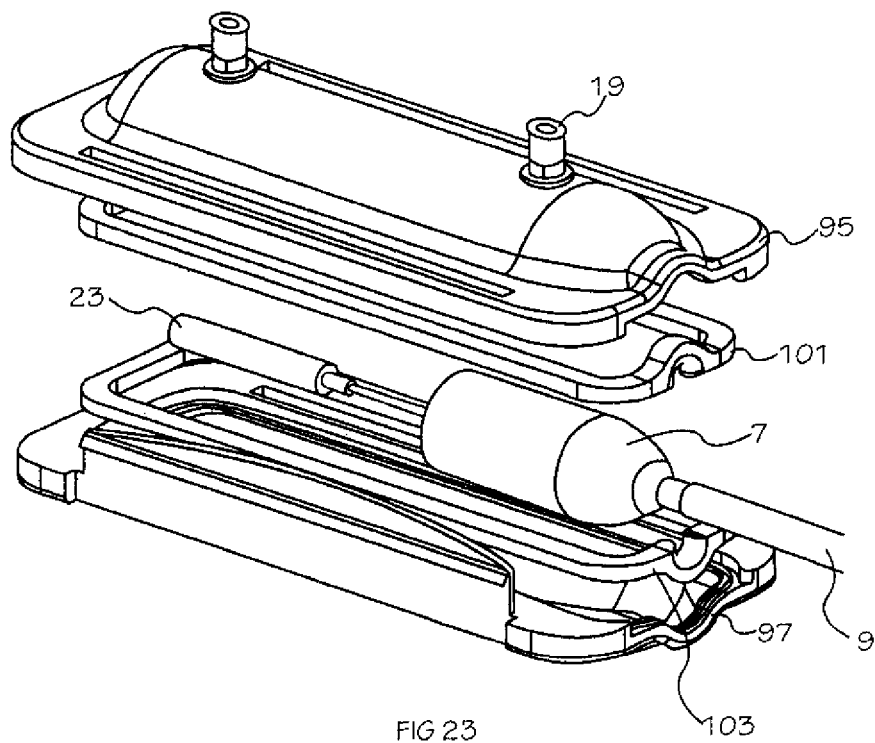
FIG. 23 shows a clam shell embodiment of a wet container for the package in an exploded view using two gaskets to seal the container.
Figure 24:
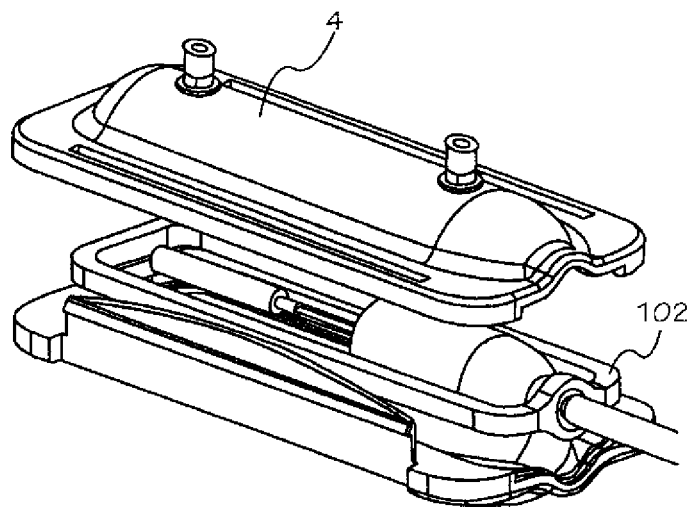
FIG. 24 depicts a clam shell embodiment of a wet container for the package in an exploded view using a single gasket to seal the container.
Figure 25:
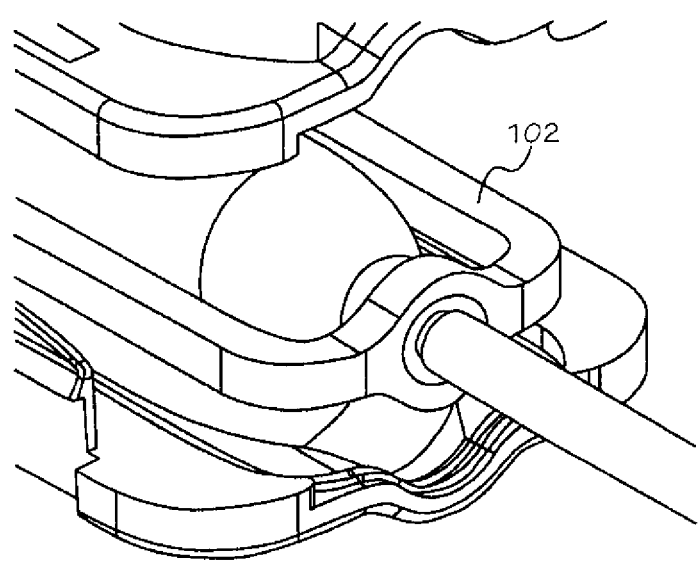
FIG. 25 shows a detail of a clam shell embodiment of a wet container for the package in an exploded view using a single gasket to seal the container.

In a further embodiment as shown in FIGS. 22 and 23, exemplary wet container 4 comprises an upper housing 95 and lower housing 97, and an upper gasket 101 and lower gasket 103 which create the seal between the wet compartment and the dry compartment of the packaging system. This embodiment is desirable because it allows the seal to be created simply by the interface between the delivery tool, gaskets, and housings. The gaskets prevent the fluid from escaping the wet compartment, thus keeping the delivery tool dry. In some embodiments the upper and lower gaskets 101 and 103 could be molded to the upper and lower housings 95 and 97, respectively. In other embodiments the gaskets could be bonded to the housings with adhesive material or maintained by interference fits. In other embodiments the housings and gaskets could remain separate, loose parts. In further embodiments the seal could be created from a single gasket 102 within housings as illustrated in FIGS. 24 and 25. Such an embodiment might require the gasket to be broken for removal from the delivery tool prior to use of the implant delivery system.

The present invention also draws on methods of packaging an implant that is pre-attached to a delivery tool used to deliver the implant to a specific location within a patient. The implant is loaded into a wet compartment of the package such that the delivery tool remains in the dry compartment of the package. In some embodiments the implant is partially stored in the wet compartments. In other embodiments the delivery tool is partially stored in the dry compartment. In further embodiments the implant is partially stored in the wet compartment and the delivery tool is partially stored in the dry compartment. The method of storing an implant pre-attached to a delivery tool allows the delivery system to be used immediately after it is removed from the packaging, such that a user subjected to the concerns associated with attaching an implant to a delivery tool in the procedure setting. This provides for a quicker, safer, and more efficient procedure.

Figure 26A:
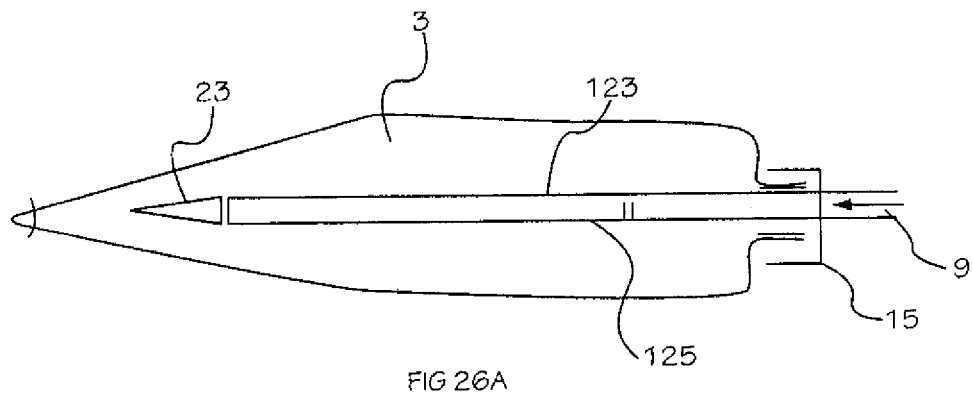
FIGS. 26A-D show a depiction of a method for introducing and removing an implant from a wet container.
Figure 26B:
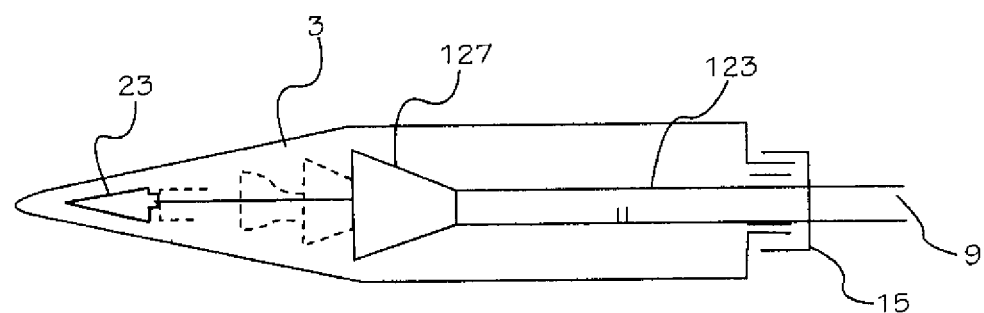
Figure 26C:
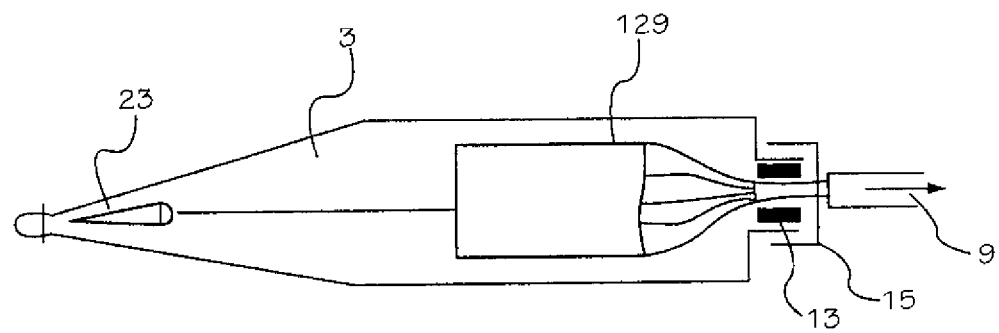

One embodiment of the packaging method is shown in FIGS. 26A-C. Sheathed implant 125 is first loaded through seal cap 15 and further into wet compartment 3. FIG. 26B illustrates the step of unsheathing the expanding implant 127 while sheath 123 is urged towards the proximal end of wet compartment 3. Once the sheath 123 has been completely removed from expanding implant 129 as shown in FIG. 26C, seal 13 can be formed using any of the examples discussed above to prevent fluid [not shown] from escaping wet compartment 3. After the seal 13 is formed, the expanded implant can be stored inside wet compartment 3, immersed in fluid [not shown], for an extended period of time as needed. The method of storing expanded implant 129 allows the implant to retain a natural and relaxed configuration during storage which allows for a more biologically functional implant to be inserted into a patient. The dual compartment design of the invention allows the implant to be retained in this relaxed state during storage while being preserved in a solution which is maintained inside the wet compartment, such that the delivery tool remains at least partially dry in the dry compartment.

Figure 26D:
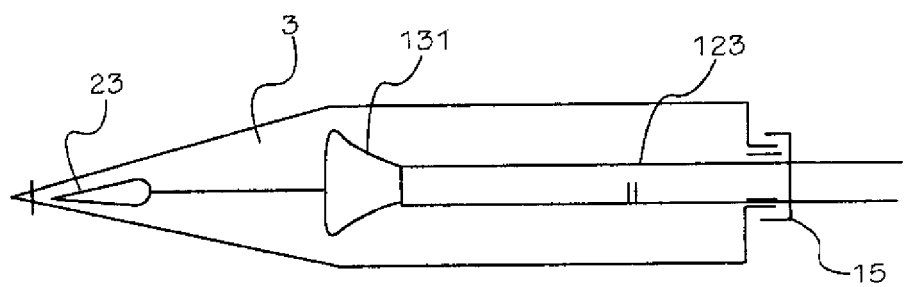

When the implant 129 is needed for use, the flushing luer part 19 as shown in FIG. 3 can be used to flush and or rinse the fluid 17 out of wet compartment 3. Referring now to FIGS. 26C-D, seal 13 can then be released in a reverse manner to any of the methods of creating the seal discussed above, or any other seal creating mechanism which may be known in the art. Once seal 13 is released, sheath 123 can then be distally slid to resheath the implant 131 until the implant is again in a fully sheathed state 125. The implant can then be removed from the wet compartment 3 and further prepared for use. The pre-attached storage allows for immediate use and eliminates the step of a user attaching an implant to a delivery tool during surgery.

It will be necessary to sterilize part of all of the implant delivery system to prevent infection when the delivery system is inserted into a patient. In some embodiments the fluid in the wet compartment in which the implant is immersed during storage may be sterilized to maintain a sterile environment for the implant during storage. In other embodiments it may be desirable to sterilize the delivery tool of the implant system, either alone or in conjunction with the fluid. Sterilization in the present invention may be by chemical, heat, irradiation, gas, or any other known means. The dual compartment design of the invention allows the implant to be stored in solution, yet provides the added benefit that the fluid may be used as a mask to radiation sterilization such that if the entire delivery system is sterilized, the implant will receive a smaller dose of sterilization than the delivery tool due to the masking effect of the fluid. This smaller dose received by the implant will reduce the risk of damage and loss of functionality of the implant components susceptible to radiation damage such as certain polymers and tissue components.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of unpacking a medical implant and delivery tool comprising:
   receiving an implant connected to a delivery tool wherein the implant is at least partially stored in a wet compartment;
   removing fluid from the wet compartment;
   altering the configuration of the implant from a first expanded configuration to a second collapsed configuration; and
   removing the implant from the wet compartment.

2. The method of claim 1, wherein the step of receiving an implant connected to a delivery tool wherein the implant is at least partially stored in a wet compartment further comprises receiving an implant connected to a delivery tool wherein the delivery tool is at least partially stored in a dry compartment.

3. The method of claim 2, further comprising removing the delivery tool from the dry compartment.

4. The method of unpacking of claim 1 wherein the implant is at least partially contained within a sheath in the second collapsed configuration and is not contained within the sheath in the first expanded configuration.

5. The method of unpacking of claim 1 further comprising washing/rinsing the implant in the wet compartment after removing fluid from the wet compartment.

* * * * *